US00PP32930P3

(12) United States Plant Patent
Larse

(10) Patent No.: US PP32,930 P3
(45) Date of Patent: Mar. 30, 2021

(54) STRAWBERRY PLANT NAMED 'CAPRICE'

(50) Latin Name: ***Fragaria* x *ananassa***
Varietal Denomination: Caprice

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 92 days.

(21) Appl. No.: 15/998,932

(22) Filed: Aug. 23, 2018

(65) Prior Publication Data

US 2019/0069457 P1 Feb. 28, 2019

Related U.S. Application Data

(60) Provisional application No. 62/550,183, filed on Aug. 25, 2017.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

U.S. PATENT DOCUMENTS

| | | | |
|---|---|---|---|
| PP16,228 | P3 | 1/2006 | Shaw et al. |
| PP25,867 | P3 | 9/2015 | Larse |
| PP31,772 | P3 | 5/2020 | Larse |

*Primary Examiner* — Kent L Bell
(74) *Attorney, Agent, or Firm* — Cooley LLP

(57) ABSTRACT

The present invention provides a new and distinct strawberry plant designated as 'Caprice' (a.k.a. '109862').

7 Drawing Sheets

Latin name of the genus and species: *Fragaria* x *ananassa.*

Varietal denomination: 'Caprice' (a.k.a. '109862').

BACKGROUND OF THE INVENTION

The present invention relates to a new and distinct strawberry plant designated as 'Caprice' (a.k.a. '109862').

'Caprice' (a.k.a. 109862) is the result of a controlled-cross between a female parent cultivar designated '109013' (not patented) and a male parent cultivar designated 'Crystalina' (U.S. Plant Pat. No. 25,867) made by the Inventor and was first fruited in Watsonville, Calif. growing fields. Following selection and during testing, the plant was originally designated '109862' and subsequently named 'Caprice'. 'Caprice' is a day-neutral plant.

This new strawberry plant was asexually reproduced via runners (stolons) by the inventor at Watsonville, Calif. Asexual propagules from the original source have been tested in Watsonville growing fields and to a limited extent, grower fields in high elevation. The properties of this plant were found to be transmissible by such asexual reproduction. This plant is stable and reproduces true to type in successive generations of asexual reproduction.

BRIEF SUMMARY OF THE INVENTION

This invention relates to a new and distinctive strawberry plant designated as 'Caprice' (a.k.a. '109862'). This plant is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish the strawberry plant 'Caprice' from known strawberry plants. In addition, this plant was confirmed, or will be confirmed to be a unique strawberry germplasm using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used.

'Albion' (U.S. Plant Pat. No. 16,228) is a commercial strawberry variety that is similar to, but distinguished from 'Caprice'. The fruit yield of 'Caprice' exceeds the yield of 'Albion' in multiple annual testing cycles performed at the breeder's test location in Watsonville, Calif. 'Caprice' presents fruits that are smaller than the fruit of 'Albion'. The cull rate 15 of marketable fruit is lower than the cull rate of 'Albion'.

When compared to the proprietary male parent, 'Caprice' has smaller fruit than its male parent. Additionally, 'Caprice' produces more fruit and is a larger plant than the male parent. When compared to the proprietary female parent, 'Caprice' is a larger, more upright plant than the female parent. Additionally, 'Caprice' has longer petioles and larger fruit than the female parent.

DESCRIPTION OF THE DRAWINGS

The accompanying color photographs depict various characteristics of the cultivar as nearly true as possible to make color reproductions.

DETAILED DESCRIPTION OF THE INVENTION

'Caprice' (a.k.a. '109862')

Figure 1:
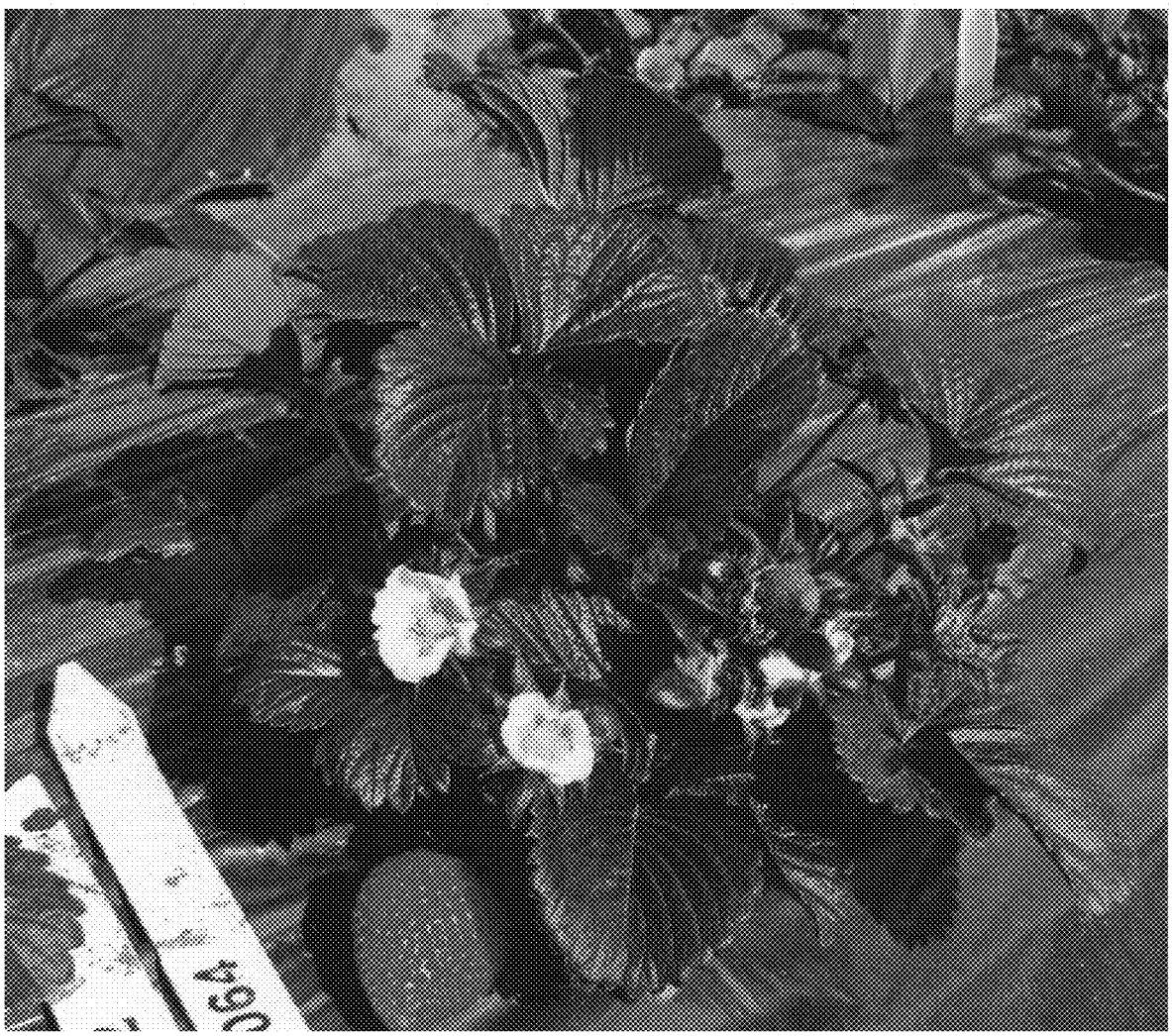
FIG. 1 shows 'Caprice' plant about 6-month old.
Figure 2:
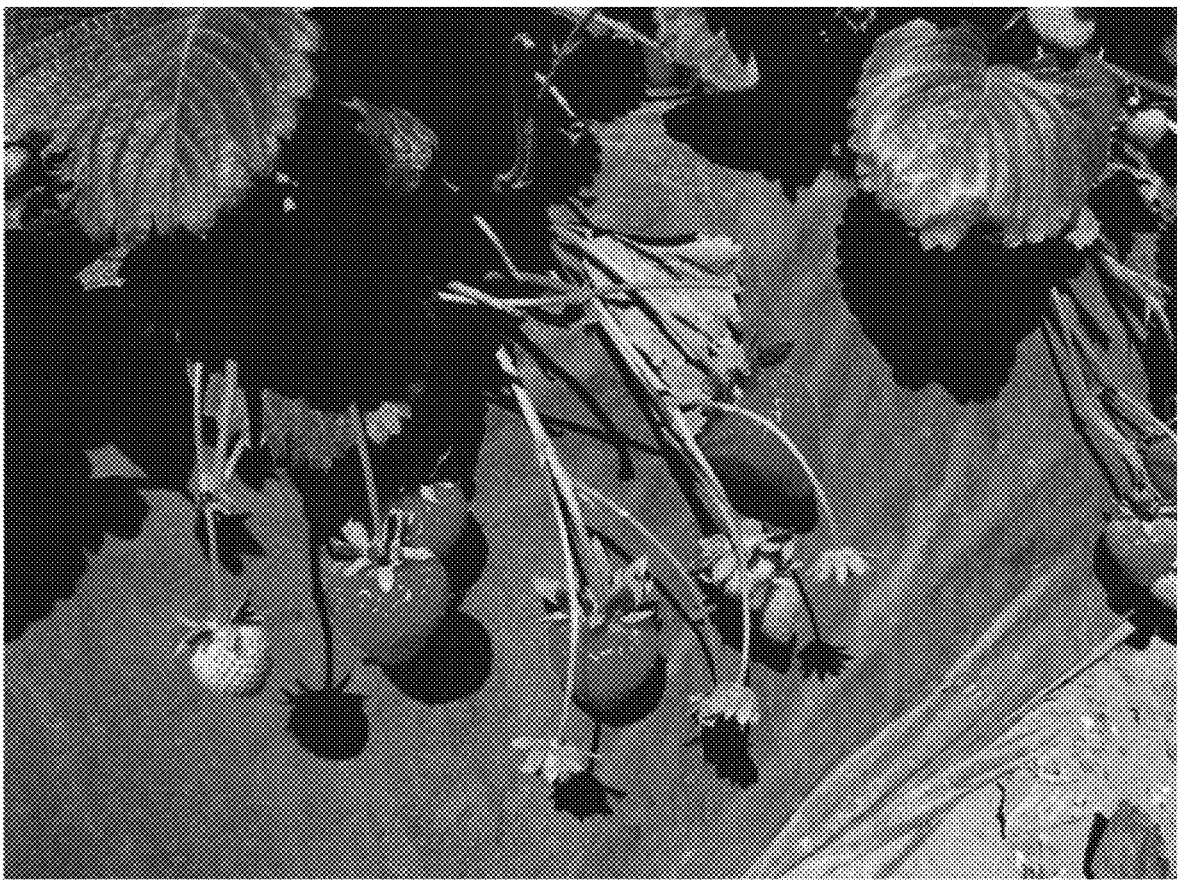
FIG. 2 shows ripe and near-ripe fruits of 'Caprice' about 8-month old.
Figure 3:
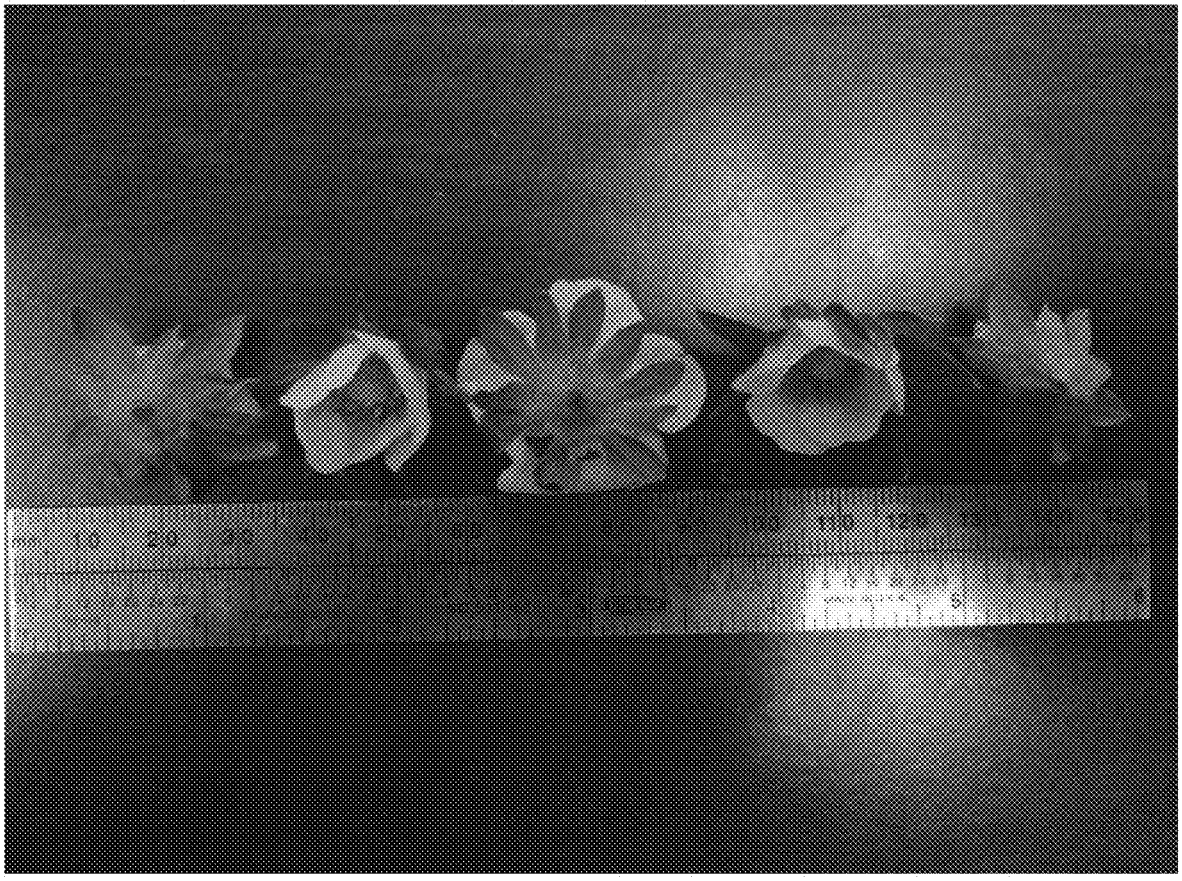
FIG. 3 shows flowers of 'Caprice'.
Figure 4:
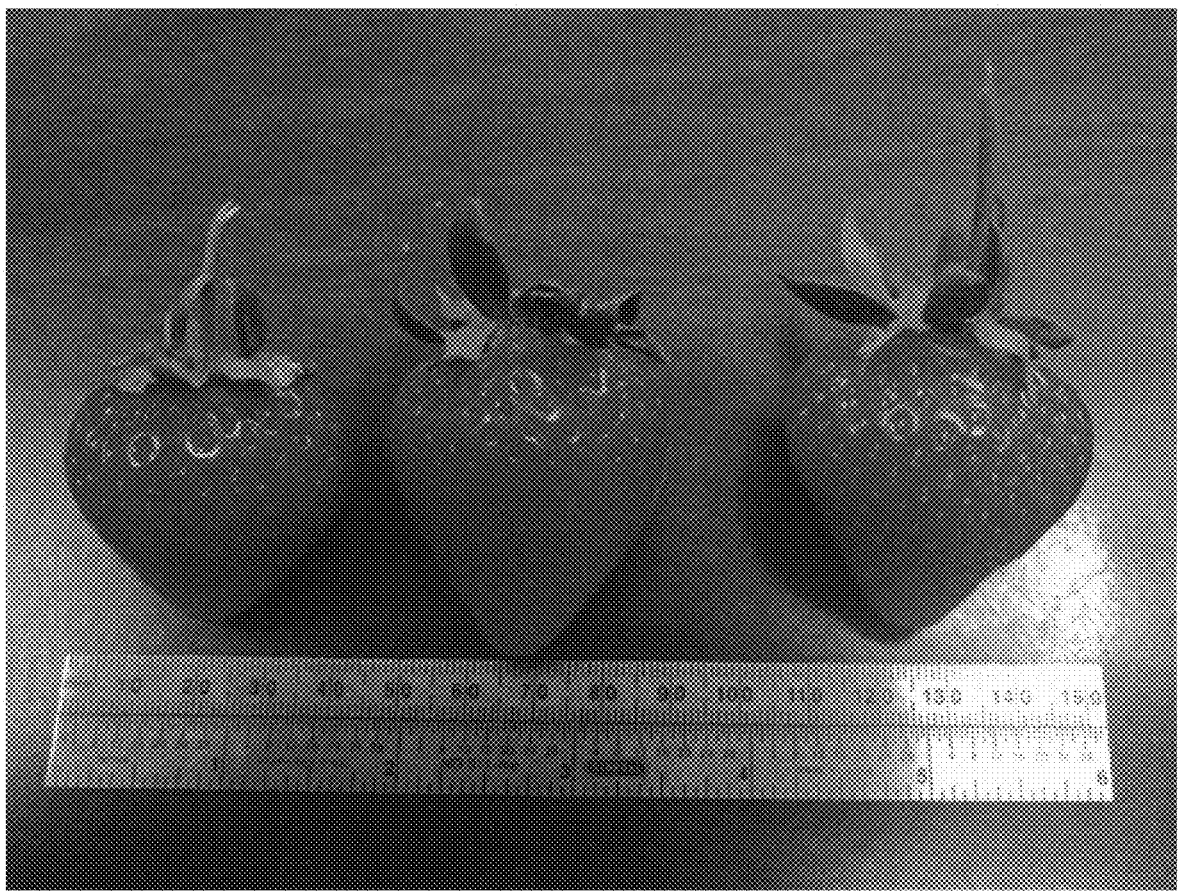
FIG. 4 shows fruits of 'Caprice'.
Figure 5:
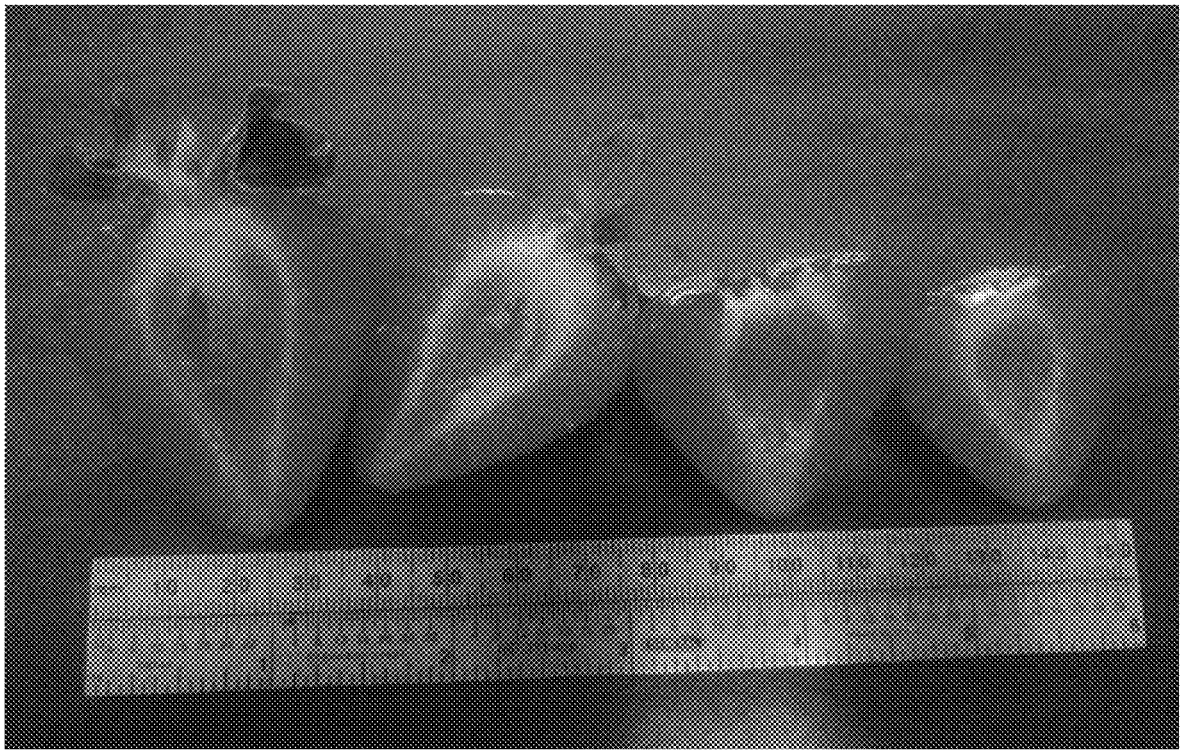
FIG. 5 shows cut fruits of 'Caprice'.
Figure 6:
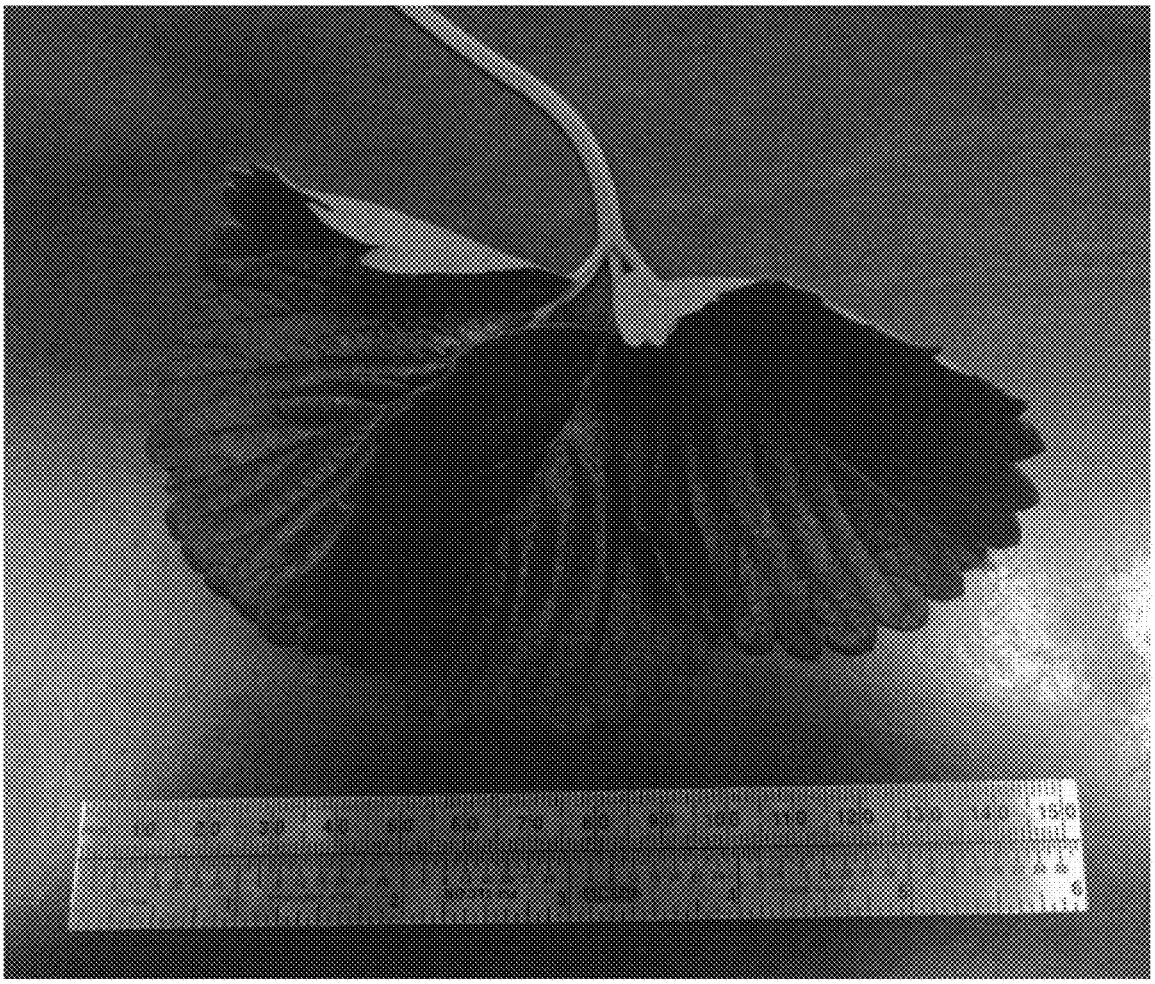
FIG. 6 shows upper leaf of 'Caprice'.
Figure 7:
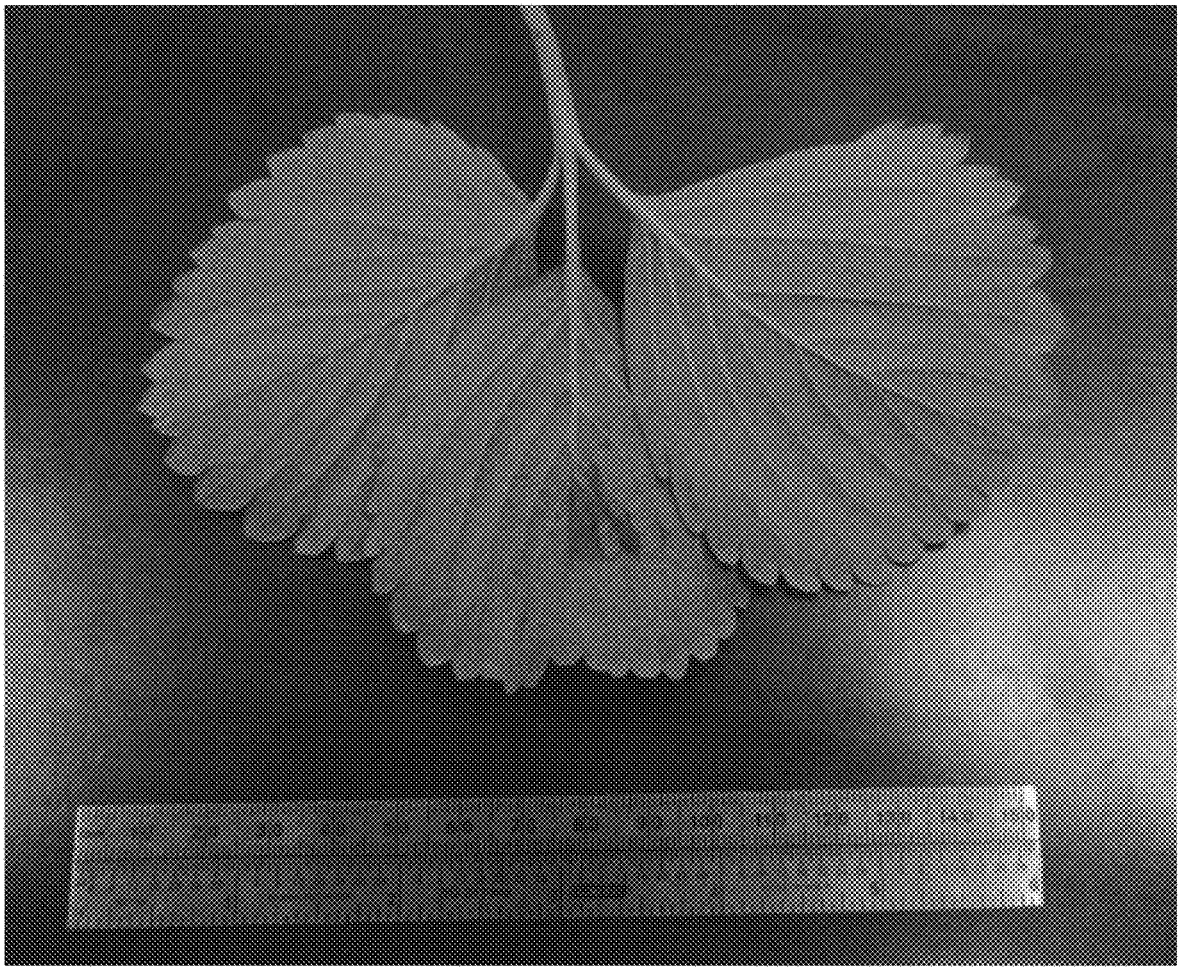
FIG. 7 shows lower leaf of 'Caprice'.

The following traits in combination distinguish strawberry variety 'Caprice' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

'Caprice' has not been observed under all possible environmental conditions, and the phenotype may vary significantly with variations in environment. The following observations, measurements, and comparisons describe this plant as grown under normal conditions in Watsonville, Calif. unless otherwise noted. The plants were 8-month old when the observation was made.

TABLE 1

'Caprice' Characteristics

| Type | Characteristic | 'Caprice' |
|---|---|---|
| General | Cross date | 2014 Jan. 17 |
| | Age of plant when described | 8 months |
| | Self fertility | Not tested |
| | Thrips susceptibility | Low |
| | Powdery Mildew susceptibility | Moderate |
| | Plant habit | Annual |
| | Plant growth habit | Upright |
| | Day length | Day neutral |
| | Planting season | Fall |
| | Root type | Fibrous and branching |
| | Root color (RHS color code) | 18C to 155B |
| | Plant Height (cm) | 35 |
| | Plant Width (cm) | 32 |
| | Density of foliage | Medium |
| | Plant vigor | Moderate to high |
| | Freezing quality | Moderate |
| | Rain/weather tolerance | Moderate |
| | Harvest ease | Moderate |
| | Crown diameter (cm) | 8.0 to 10.0 |
| Leaf | Trifoliate leaf length (cm) | 14.5 to 16.0 |
| | Trifoliate leaf width (cm) | 13.0 to 14.0 |
| | Trifoliate leaf shape | Flat |
| | Leaf blistering | Weak |
| | Leaf glossiness | Strong |
| | Leaf variegation | Absent |
| | Number of leaflets per Leaf | 3 |
| | Terminal leaflet width (mm) | 70 to 80 |
| | Terminal leaflet length (mm) | 77.5 |
| | Terminal leaflet length/width ratio | 0.9 to 1.03 |
| | Number of teeth/terminal leaflet | 25 |
| | Shape of terminal leaflet | Orbicular |
| | Shape of the terminal leaflet apex | Rounded |
| | Shape of the terminal leaflet base | Obtuse to rounded |
| | Shape of terminal leaflet in cross-section | Straight |
| | Shape of terminal leaflet margin | Serrate to crenate |
| | Color of upper side of leaflets (RHS color code) | 137A |

TABLE 1-continued

'Caprice' Characteristics

| Type | Characteristic | 'Caprice' |
|---|---|---|
| | Color of lower side of leaflets (RHS color code) | 137C |
| Limbs | Petiole length (cm) | 26.5 |
| | Petiole diameter (mm) | 3.68 |
| | Petiole texture | Puberulous |
| | Petiole pubescence medium to dense | Medium to dense |
| | Petiole pose of hairs horizontal | Horizontal |
| | Petiole color (RHS color code) | 145A |
| | Petiolule length (cm) | 1.5 |
| | Petiolule diameter (mm) | 2.32 |
| | Stipule number | 2 per petiole |
| | Stipule length (cm) | 2.5 |
| | Stipule width (cm) | 0.7 |
| | Stipule shape | Lanceolate |
| | Stipule apex | Acuminate |
| | Stipule margin | Entire |
| | Stipule base | Truncate |
| | Stipule texture | Puberulous |
| | Stipule pubescence | Medium to dense |
| | Stipule anthocyanin | Weak |
| | Stipule color (RHS color code) | 149D |
| | Stipule anthocyanin color (RHS color code) | 58B to 55A |
| | Pedicel length (cm) | 11.0 to 22.0 |
| | Pedicel diameter (mm) | 2.0 to 2.6 |
| | Pedicel color (RHS color code) | 145A |
| | Pedicel texture | Puberulous |
| | Pedicel pubescence | Sparse |
| | Peduncle size | Medium |
| | Peduncle length (cm) | 7.0 to 14.0 |
| | Peduncle diameter (mm) | 2.59 to 3.65 |
| | Peduncle texture | Puberulous |
| | Peduncle pubescence | Medium |
| | Attitude of hairs on petiole and pedicel | Upwards |
| Inflorescence | Time of flowering (50% of plants in bloom) | March to April |
| | Lastingness of bloom | 7 to 10 days |
| | Inflorescence position relative to foliage | Above |
| | Number of flowers per inflorescence | 3 to 6 |
| | Flower arrangement of petals | Touching |
| | Flower diameter (cm) | 2 |
| | Flower bud shape | Globose, obovate |
| | Flower bud length (cm) | 1.7 to 2.5 |
| | Flower bud diameter (cm) | 1.1 |
| | Flower bud texture | Puberulous |
| | Flower bud pubescence | Dense |
| | Flower bud color (RHS color code) | 145B |
| | Petal length (cm) | 1.3 |
| | Petal width (cm) | 1.5 |
| | Petal length/ width ratio | 0.87 |
| | Number of Petal per flower | 5 to 6 |
| | Upper Petal color (RHS color code) | 155C |
| | Lower Petal color (RHS color code) | 155C |
| | Petal shape | Orbicular |
| | Petal apex | Rounded |
| | Petal margin | Entire |
| | Petal base shape | Concave |
| | Corolla depth (mm) | 9 to 13 |
| | Corolla diameter (cm) | 2 |
| | Floral Calyx diameter (cm) | 3 to 4 |
| | Calyx diameter relative to corolla | Larger |
| | Inner calyx diameter relative to outer calyx | Equal to smaller |
| | Sepal number per flower | 10 |
| | Sepal length (cm) | 1.1 |
| | Sepal width (cm) | 0.7 |
| | Sepal shape | Elliptical |
| | Sepal apex | Convex |
| | Sepal margin | Entire |
| | Upper sepal texture | Smooth |
| | Lower sepal texture | Puberulous |
| | Lower sepal pubescence | Medium |

TABLE 1-continued

'Caprice' Characteristics

| Type | Characteristic | 'Caprice' |
|---|---|---|
| | Upper sepal color (RHS color code) | 137A |
| | Lower sepal color (RHS color code) | 137C |
| | Pistil number | 121 to 286 |
| | Pistil length (mm) | 2.0 to 2.25 |
| | Shape of stigma | Capitate |
| | Color of stigma (RHS color code) | 12A |
| | Length of style (mm) | 2 |
| | Color of style (RHS color code) | 4A |
| | Color of the ovary (RHS color code) | 145A |
| | Length of the stamens (mm) | 4 |
| | Number of stamen | 23 to 25 |
| | Anther diameter (mm) | 1.0 to 1.25 |
| | Anther length (mm) | 1.0 to 2.0 |
| | Shape of anther | Dorsifixed |
| | Size of anther | Medium |
| | Color of anther (RHS color code) | 12A |
| | Amount of pollen | Medium |
| | Color of pollen (RHS color code) | 12A |
| | Length of filament (mm) | 4 |
| | Color of filament (RHS color code) | 149D |
| Stolon | Stolon length (cm) | 33 to 77 |
| | Stolon number | 2 to 5 |
| | Stolon shape | Filiform |
| | Stolon anthocyanin (RHS color code) | 181A |
| | Stolon thickness | Medium |
| | Stolon texture | Puberulous |
| | Stolon pubescence | Sparse to medium |
| | Widest diameter of stolon at leaf attachment (mm) | 4.62 |
| | Stolon color (RHS color code) | 145A |
| Fruit | Number of fruit per truss | 2 to 4 |
| | Fruiting truss length (cm) | 7.0 to 14.0 |
| | Fruiting truss diameter (mm) | 3.50 to 7.65 |
| | Fruiting truss attitude | Prostrate |
| | Shape difference between primary & secondary fruits | No shape difference |
| | Predominant fruit shape | Conic |
| | Fruit calyx diameter (cm) | 3.3 to 5.3 |
| | Color of calyx (RHS color code) | 136A |
| | Position of calyx | Even |
| | Level of adherence of calyx | Medium |
| | Pose of calyx segments | Spreading to reflexed |

TABLE 1-continued

'Caprice' Characteristics

| Type | Characteristic | 'Caprice' |
|---|---|---|
| | Size of calyx in relation to fruit | Equal |
| | Fruit length (cm) | 34.1 |
| | Fruit width (cm) | 29.5 |
| | Fruit length/width ratio | 1.16 |
| | Fruit skin color (RHS color code) | 41A |
| | Fruit flesh color excluding core (RHS color code) | 44A |
| | Fruit core color (RHS color code) | 41A |
| | Fruit weight (g) | 22.7 |
| | Relative fruit size | Medium |
| | Fruit glossiness | Medium |
| | Firmness of flesh | Medium |
| | Evenness of flesh color | Nearly even |
| | Hollow core length (cm) | 1.1 to 2.7 |
| | Hollow core width (cm) | 0.8 to 1.5 |
| | Hollow core length/width ratio | 1.38 to 1.80 |
| | Hollow core size | Medium |
| | Width of band without of achenes | Narrow |
| | Position of achenes in relation to skin surface | Below surface |
| | Achene color (RHS color code) | 145B |
| | Achenes per fruit | 288 |
| | Achene weight (g) | 0.17 |
| | Surface/skin texture | Smooth |
| | Texture when tasted | Medium |
| | Flavor | Sweet |
| | Sweetness (brix) | 10 |
| | Acidity (pH) | 3.45 |
| | Type of bearing | Day neutral |
| | Time of fruit ripening | May to June |
| | Harvest maturity (50% of plants with ripe fruit) | June |
| | First picking harvest | Mid-March |
| | Last picking harvest | Mid-September |
| | Appearance score | 4 |
| | Storage longevity | 8 to 10 days |
| | Yield (kg per plant per season) | 2.791 |
| | Cull rate: 100% - Marketable yield % | <15% |

The invention claimed is:

1. A new and distinct cultivar of strawberry plant named 'Caprice' substantially as shown and described herein.

* * * * *